United States Patent [19]

Regtop et al.

[11] Patent Number: 5,310,936

[45] Date of Patent: May 10, 1994

[54] PREPARATION OF DIVALENT METAL SALTS OF INDOMETHACIN

[75] Inventors: Hubertus L. Regtop, Scotland Island NSW; John R. Biffin, Berrima NSW, both of Australia

[73] Assignee: Biochemical Veterinary Research Pty. Ltd., Mittagong, Australia

[21] Appl. No.: 773,601

[22] Filed: Jan. 15, 1992

[30] Foreign Application Priority Data

May 22, 1989 [AU] Australia ............... PJ4328

[51] Int. Cl.$^5$ ........................................ C07D 209/28
[52] U.S. Cl. ................................ 548/501; 548/500; 548/420
[58] Field of Search ............... 514/420; 548/500, 501

[56] References Cited

FOREIGN PATENT DOCUMENTS

| | | |
|---|---|---|
| 245126 | 11/1987 | European Pat. Off. . |
| 405602 | 1/1991 | European Pat. Off. . |
| 73044 | 12/1977 | Romania . |
| 73045 | 12/1977 | Romania . |
| 448955 | 11/1917 | Spain . |

OTHER PUBLICATIONS

Weser et al., "Structure of Cu$_2$ (indomethacin) and the reaction with superoxide in aprotic systems," Biochim. Biphys. Acta, 631, 232–45, (1980).
Ivancheva, et al., Acta Physiol. Pharmacol. Bulgaria, 14, 52 (1988).
Lewis et al., Agents Actions Supp., 1981, 8, 339–58.
Singla et al., Int'l J. Pharmaceutics, 60, 27–33 (1990).
Flower et al., The Pharmacological Basis Of Therapeutics, pp. 674–704 (Gilman et al. eds. 1985).
Shay et al., Gasroenterology, 5, 43–61 (1945).
Sorenson, J. Med. Chem., 19, 135–48 (1976).
Sorenson et al., Biol. Trace Element Res., 5, 257–73 (1983).
Barbu et al., Chemical Abstracts, vol. 100, No. 13, Abstract No. 103177 (Mar. 26, 1984).
Barbu et al., Chemical Abstracts, vol. 99, No. 13, Abstract No. 105123 (Sep. 26, 1983).
Rusanov et al., Chemical Abstracts, vol. 109, No. 17, Abstract No. 142549 (Oct. 24, 1988).
Rusanov et al., Acta Physiol. Pharmacol. Bulg., 1988, 14(1), 52–9.
Ogiso et al., Chemical And Pharmaceutical Bulletin, vol. 36, No. 2, 1988, pp. 757–762.
Lewis et al., Chemical Abstracts, vol. 96, No. 17, Abstract No. 135522 (Apr. 26, 1982).
Lewis et al., Agents Actions Supp., 1981, 8 (Trace Elem. Pathog Treat. Inflammation), 339–58.
Adsara Dalmau, Chemical Abstracts, vol. 89, No. 21, Abstract No. 186070 (Nov. 20, 1978).
Singla et al., Chemical Abstracts, vol. 113, No. 7, Abstract No. 65154 (Aug. 13, 1990).
Singla et al., Int. J. Pharm., 1990, 60(1) 27–33.

Primary Examiner—David B. Springer
Attorney, Agent, or Firm—Willian Brinks Hofer Gilson & Lione

[57] ABSTRACT

The present invention provides a method for the treatment of inflammation and pain in a mammal requiring such treatment, comprising administering to said mammal an anti-inflammatory and analgesically effective amount of an indomethacin salt of a divalent metal capable of forming a stable complex with indomethacin, or of a pharmaceutical composition comprising said indomethacin salt together with a pharmaceutically acceptable carrier, diluent and/or excipient. The present invention also provides a process for the preparation of an indomethacin salt of a divalent metal capable of forming a stable complex with indomethacin comprising forming a solution by dissolving indomethacin and a salt of said divalent metal in a tertiary amide or cyclic tertiary amide, adding a $C_{1-4}$ alkanol or $C_{3-6}$ ketone to the solution to precipitate the indomethacin metal salt and separating the indomethacin metal salt precipitate from the solution. The present invention still further provides a pharmaceutical composition for alleviating inflammation and pain comprising an anti-inflammatory and analgesically effective amount of salts of indomethacin produced by the process of the invention together with a pharmaceutically acceptable carrier, diluent and/or excipient.

21 Claims, No Drawings

PREPARATION OF DIVALENT METAL SALTS OF INDOMETHACIN

The present invention relates to a process for the preparation of metal salts of indomethacin, and more particularly to an efficient process for the preparation of copper indomethacin.

The invention also relates to a composition containing a metal salt indomethacin and more particularly to an oral composition containing copper indomethacin.

The invention further relates to a method for the treatment of various conditions in mammals and in particular to shin soreness and other musculo-skeletal inflammation in mammals including man and more particularly to the treatment of those conditions in horses.

BACKGROUND ART

Copper acetate has been observed to be more active than hydrocortisone in the carageen foot oedema model of inflammation. It has been suggested that administration of copper acetate results in the formation of copper chelates in vivo and it is the chelate that is responsible for the anti inflammatory activity.

Copper complexes have been shown by Sorenson (1976) to be anti-arthritic.

The number of pharmacological activities of copper complexes in the model of chronic diseases continues to increase at a rapid rate (Sorenson (1983)).

It has also been reported that copper complexes have anti-inflammatory, anti-ulcer, anti-convulsive, anti-cancer and anti-diabetic activities (Sorenson (1983)).

(Copper II)$_2$ (acetyl salicylate)$_4$, (copper II)$_2$ [1-(p-chloro benzoyl)-5-methoxy-2-methylindole-3-acetate]$_4$ (hereinafter referred to as copper indomethacin), copper II (salicylate)$_2$ have been found to be more effective as analgesics than their parent acids in the writhing mouse and adjuvant arthritic rat pain models. Copper indomethacin has also been found to be as effective as morphine in both laboratory models.

Prior to this invention, preparations of copper indomethacin have been only laboratory items of no apparent benefit to man or domestic animals. The inventors have shown a clinically useful and safe drug.

Copper indomethacin has been found to be more efficient than indomethacin on its own and is also more efficient than phenylbutazone.

Present medical treatment of shin soreness and other musculo-skeletal inflammation in horses involves mainly administration of nonsteroidal anti-inflammatory drugs (NSAIDs). For example, phenylbutazone has been the definitive drug used in the race horse industry for many years. However phenylbutazone has a long and unpredictable excretion and while the pharmacological actions of this drug may be complete within 24 hours, undesirable detection may continue in plasma and urine for long periods after cessation of treatment. This is of importance to animals required to compete drug-free. Furthermore, phenylbutazone has established and widely reported gut toxicity in the horse.

Indomethacin itself has a half-life of 2 to 11 hours which means it must be administered 2 to 3 times daily to be effective (Flower, R. J., Moncado, S., and Vane, J. R. (1985) Analgesic-Antipyretics and Anti-Inflammatory Agents: Drugs employed in the treatment of gout. In: "The Pharmacological Basis of Therapeutics" 7th Ed. Eds Gilman, A. G., Goodman, L. S., Rall, T. W., and Murad, F. MacMillan, New York, 1985).

While it is known that indomethacin has an anti-inflammatory action, it is also known that it causes gastro-intestinal reaction in some mammals e.g. dogs and humans. These reactions include single or multiple ulcerations of the oesophagus, stomach and duodenum. Attempts to reduce these gastro-intestinal effects have been made by taking the oral drug immediately after meals, with food, milk or antacids, or antiulcer compounds.

Furthermore, NSAIDs have an analgesic effect which is partly a result of and independent of, and partly dissociated from, their anti-inflammatory action. This dissociation varies from drug to drug. Thus analgesia obtained from phenylbutazone and, to a lesser extent indomethacin is primarily a result of its anti-inflammatory action.

DISCLOSURE OF INVENTION

According to one broad form of this invention there is provided a method for the treatment of inflammation and pain in a mammal requiring such treatment, comprising administering to said mammal an anti-inflammatory and analgesically effective amount of an indomethacin salt of a divalent metal capable of forming an stable complex with indomethacin, or of a pharmaceutical composition comprising said indomethacin salt together with a pharmaceutically acceptable carrier, diluent and/or excipient.

According to another broad form of this invention there is provided a process for the preparation of an indomethacin salt of a divalent metal capable of forming a stable complex with indomethacin comprising forming a tertiary amide (dialkyl amide of a lower alkanoic acid) of the following formula

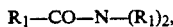

or in an N-substituted lactam of the following formula

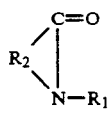

wherein $R_1$ is an alkyl having from 1 to 4 carbon atoms, and each $R_1$ may be the same or different, and $R_2$ is a cycloalkyl having from 3 to 5 carbon atoms solution by dissolving indomethacin and a salt of said divalent metal in a cyclic tertiary amide, adding a $C_{1-4}$ alkanol or $C_{3-6}$ ketone to the solution to precipitate the indomethacin metal salt and separating the indomethacin metal salt precipitate from the solution.

According to yet another broad form of this invention there is provided a pharmaceutical composition for alleviating inflammation and pain comprising an anti-inflammatory and analgesically effective amount of salts of indomethacin produced by the process of the invention together with a pharmaceutically acceptable carrier, diluent and/or excipient.

The divalent metal salt of indomethacin or the pharmaceutical composition may be administered orally, parenterally, rectally, topically or as a topical spray as described below.

The divalent metal is preferably copper, zinc, cobalt or nickel and is more preferably copper.

The salt is preferably the acetate and more preferably the acetate monohydrate.

The most preferred indomethacin salt is cupric acetate monohydrate.

Generally the process for the preparation of a metal salt of indomethacin comprises adding a solution of indomethacin to a solution of a metal acetate monohydrate and warming; adding a $C_{1-4}$ alkanol or $C_{3-6}$ ketone with agitation to the solution, allowing the solution to stand, harvesting resultant precipitate, washing with either the same alkanol or ketone used in the last addition step and drying.

The tertiary amide or $C_4$-$C_5$ imide is generally dimethylformamide, N-methylpyrrolidone and/or dimethyl acetamide.

Typically the solution of indomethacin is heated prior to addition to the divalent metal salt solution to between 30° and about 90° C. and more preferably heated to about 50° C.

The mixture of indomethacin and the acetate monohydrate is preferably warmed to between about 50° and about 90° C. and is preferably warmed to about 80° C.

The alkanol or ketone is preferably added with agitation to the solution of indomethacin and metal salt.

The alkanol which is added to the mixture of indomethacin and the acetate monohydrate and is subsequently used to wash the precipitate is preferably ethanol or methanol and more preferably ethanol.

$C_3$- alkanol also includes propanol and isopropanol and $C_4$- alkanol includes butanol, sec butanol and tert butanol.

An example of a $C_{3-6}$ ketone is acetone.

The period for which the resultant solution is allowed to stand is about eight hours to about four days and is preferably about one day.

The compositions of the present invention may be administered orally, parenterally, rectally, or topically or as a topical spray containing conventional, non-toxic, pharmaceutically acceptable carriers, diluents, and/or excipients as desired.

Liquid dosage forms for oral administration may include pharmaceutically acceptable emulsions, syrups, solutions, suspensions, and elixirs containing inert diluents commonly used in the art, such as water. Such compositions may also comprise wetting agents, emulsifying and suspending agents, and sweetening, flavoring, and perfuming agents including sugars such as sucrose, sorbitol, fructose etc, glycols such as polyethylene glycol, propylene glycol etc, oils such as sesame oil, olive oil, soybean oil etc, antiseptics such as alkylparahydroxybenzoate etc, and flavours such as strawberry flavour, peppermint etc.

The oral composition may be present as a paste which is the preferable presentation when administered to horses.

If the preparation is presented as a paste, the copper indomethacin is preferably mixed in a thickening agent and preservative. A preferred thickening agent is carbopol and preferred preservatives are sodium propyl hydroxybenzoate or methyl paraben and propyl paraben.

Preferably the amount of copper indomethacin in the paste administered is in the range of from about 0.03 to about 0.5 and preferably from about 0.1 to about 0.2 mg per kg of a mammal. The method of treatment of the invention may also be applied to the following mammals: man, horses, dogs, and any other domestic animal.

Solid dosage forms for oral administration may include capsules, tablets, pills, powders, and granules. In such solid dosage forms, copper indomethacin may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

When the preparation is presented as a tablet, any well known compound which increases the flow properties of the preparation is suitable and may be disodium phosphate or magnesium stearate, and preferably is disodium phosphate.

Parenteral as used herein includes subcutaneous injections, intravenous, or intramuscular injection, or infusion techniques.

When present as an injectable preparation, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions can be prepared as suppositories for rectal administration by mixing the composition with a suitable non-irritating excipient such as cocoa butter and polyethylene glycols which are solid at ordinary temperatures but liquid at the rectal temperature and will therefore melt in the rectum and release the drug.

Sore feet; bursitis; inflammation of joints; minor sprains and muscle soreness; splint exostosis; navicular disease; ringbone (non-articular); osselets (non-articular); back problems and prevention of serious injuries in horses in training and racing, may be treated with preparations of this invention.

It has been found that the inventor's formulation of copper indomethacin has a half-life of 23 to 25 hours thus making a single daily dose effective. Additionally, copper indomethacin has a potent independent analgesic effect independent of the analgesic effect resulting from the anti-inflammatory action as phenylbutazone and indomethacin itself.

It has surprisingly been found by the inventors that their formulation of copper indomethacin is effectively metabolised and undesirable urine levels are undetectable 72 hours after the last dose, for example, in horses. Preliminary trials indicate that this also holds true for humans and greyhounds.

It has been found by the inventors that their formulation of copper indomethacin is relatively non-toxic to the gut of dogs at far higher than therapeutic levels, while the same dose of indomethacin is severely toxic.

It has also been found by the inventors that a $5\times$ effective dose of their formulation is non-toxic to the gut and central nervous system (CNS) of horses, while a $1\times$ and $5\times$ effective dose of phenylbutazone is toxic to the gut, and a $5\times$ effective dose of indomethacin is toxic to the CNS.

It has also been found by the inventors that the formulation of copper indomethacin has significant non-ulcerogenic activity when tested for anti-ulcer activity in the Shay ulcer model (Shay, 1945).

BEST MODE AND OTHER MODES FOR CARRYING OUT THE INVENTION

An effective amount of copper indomethacin to achieve a desired level of analgesia and decrease in inflammation is administered orally to a horse. The composition for this purpose is presented to the horse as a paste which is prepared as follows: Carbopol is dissolved in distilled water. Sodium propyl hydroxybenzoate or methyl paraben and propyl paraben are then added to the carbopol mixture. The mixture is then heated to achieve dissolution of the three compounds. The pH is then adjusted with alkali to a value of between about 5.5 and about 6.5 which causes the thickness and viscosity of the carbopol to increase to the extent that a paste is formed.

The copper indomethacin is mixed with the paste mechanically to form a homogeneous smooth green-blue composition.

The specific dose level for a particular horse will depend on a variety of factors including age, general health, sex, diet, body weight and time of administration.

The present invention will now be described with reference to the following examples which should not be construed as limiting on the scope thereof.

EXAMPLE 1

Preparation of Copper Indomethacin

To a warm (about 50° C.) solution of 142 g of indomethacin in dimethylformamide (200 ml) was added a solution of cupric acetate monohydrate (40 g) in dimethylformamide (250 ml) and heated to 80° C. Ethanol (2.5 l) was added to the mixture with vigorous shaking and the deep green solution kept for about 1 day during which time copper indomethacin separated as a microcrystalline green powder. The mixture was filtered under vacuum and the green product washed exhaustively with ethanol (1 l), dried at room temperature overnight and further dried at 100° for 3 hours. Yield was 145 g (79.6%) which represented complexing of 7.1 g indomethacin per 100 ml solute.

EXAMPLE 2

Presentation of Copper Indomethacin as a Paste

Carbopol was dissolved in distilled water to a concentration of 1%. Methyl paraben and propyl paraben were added to a final concentration of 0.3% and 0.1% respectively; or sodium propyl hydroxybenzoate added to a final concentration of 0.45%. The mixture was heated to dissolve the above compounds. Sodium hydroxide was then added to adjust the pH to between about 5.5 to about 6.5. At this pH the thickness and viscosity of the carbopol increased dramatically to form a paste.

The copper indomethacin was then added and the composition mechanically mixed to form a smooth green-blue paste. It is necessary to add copper indomethacin after the paste has formed since addition prior to pH adjustment would prevent cross-linking of carbopol and make formation of a paste impossible.

EXAMPLE 3

Presentation of Copper Indomethacin as Tablets

Copper indomethacin (200 mg) was added to disodium phosphate (300 mg) or dipac (300 mg) and magnesium stearate (5 mg). This was then mixed to a uniform powder and added to a rotary tablet maker.

EXAMPLE 4

Presentation of Copper Indomethacin as a Topical Preparation

Copper indomethacin (1 g) and dimethyl sulphoxide (DMSO) (20 ml) was thickened by addition of glycerol (20 ml) and solid carbopol (60 g), prepared as in Example 2. This was blended into a paste which was able to be used as a topical preparation.

EXAMPLE 5

Absorption of Copper Indomethacin Paste 4 mares, A,B,C and D, bodyweight 420–455 Kg, were administered 200 mg copper indomethacin by oral paste and blood taken for analysis by HPLC one hour later.

| HORSE | COPPER INDOMETHACIN (ng/ml) |
| --- | --- |
| A | 140 |
| B | 210 |
| C | 81 |
| D | 88 |

EXAMPLE 6

Toxicity and Efficacy of Copper Indomethacin Paste

Four mares were administered 200 mg of copper indomethacin daily for 7 days and observed for changes in clinical signs. No effects were noted in mares A, B, and D. Mare C had sustained a lacerated hoof, heel and coronet between example 5 and example 6, and was unable to bear weight on the limb. By day 3 she was sound, and by day 9 severely lame again.

EXAMPLE 7

Bioavailability Studies on Horses

Horses were dosed with 200 mg of copper indomethacin in a paste of 1% carbopol in 0.3% methyl paraben and 0.1% propyl paraben, given orally. Indomethacin was detected in the urine and plasma of horses as follows.

| TIME (hours) | COPPER INDOMETHACIN ($\mu$g/ml urine) | PLASMA (ng/ml) |
| --- | --- | --- |
| 1.5 | 1.5 | 105 |
| 3 | 2.5 | 111 |
| 6 | 3.4 | 130 |
| 9 | 8.2 | 107 |
| 24 | 1.5 | 68 |
| 36 | 0.3 | 24 |
| 48 | 0.02 | 6 |
| 72 | ND | ND |

The urine concentration of copper indomethacin was highest 9 hours after administration. After 48 hours the concentration was only 0.024 $\mu$g/ml and could not be detected in the urine after 72 hours.

Analytical method were developed using GLC to allow quantification of copper indomethacin in equine plasma and urine.

EXAMPLE 8

Clinical Trails

Clinical trials on racehorses were conducted using copper indomethacin paste. The trial was conducted over a period of 5 months. During this period 1000 doses each of phenylbutazone, indomethacin and copper indomethacin were administered orally. The conclusions from the trial are:

1. A 200 mg dose of copper indomethacin has comparable clinical anti-flammatory effect to a 1 gm dose of phenylbutazone.

2. 200 gm of copper indomethacin has a superior and more reliable effect compared to 200 mg of indomethacin.

3. There have been no observed side effects in the horses receiving copper indomethacin.

EXAMPLE 9

Indications Trial

18 Racehorses in training having clinical indications expected to respond to phenylbutazone, were given copper indomethacin instead. The responses were graded "poor" if there was no response, "fair" if the clinical response was comparable or inferior to that expected from phenylbutazone, and "good" if the response was superior to the expectation had phenylbutazone been used. 14 responses were graded "good" and 4 "fair". The clinical indications where the drug was rated "good" included bruised tendon, arthritis, pedal osteitis, navicular disease, myositis, shin-soreness and osteochondritis.

A summary of the results are as follows:

| Horse No. | Period of Administration | Dosage | Indication | Response |
|---|---|---|---|---|
| 1 | 4 days | A | Bruised tendon (SDF) | Good |
| 2 | weeks | B | Pedal osteitis | Good |
|   | Lameness recurred when treatment stopped. | | | |
| 3 | weeks | B | Navicular disease | Good |
| 4 | 4 days | A | Jarred fetlocks | Good |
| 5 | weeks | B | Carpal arthritis | Good |
| 6 | weeks | B | Pedal osteitis | Good |
| 7 | weeks | B | Saccro-iliac subluxation | Fair |
| 8 | 4 days | B | Muscle soreness | Good |
| 9 | 4 days | B | Carpal arthritis | Good |
| 10 | weeks | B | Fetlock arthritis | Good |
| 11 | weeks | B | Shin soreness | Good |
| 12 | 4 days | A | OCD—shoulder | Good |
| 13 | 4 days | A | Acute sesamoiditis | Fair |
| 14 | weeks | B | Shin soreness | Fair-Good |
| 15 | 4 days | B | Muscle injury | Good |
| 16 | weeks | B | Post laminits foot soreness & fetlock injury | Good |
| 17 | weeks | B | Navicular Disease | Good |
| 18 | 4 days | B | Carpal Injury-Cartilage only | Fair |

DOSAGE
A = 200 mg copper indomethacin/6 g paste twice daily; B = 200 mg/6g paste daily.

EXAMPLE 10

Comparative Toxicity Trial in Horses

Melaena Index (measurement of occult blood in the faeces) was used to compare gastro-intestinal toxicity of the inventors' formulation of copper indomethacin with phenylbutazone in an identical paste base. Dosage range for both drugs was from normal therapeutic dose to 5× therapeutic dose. A control group received no medication. A positive index indicates gastro-intestinal toxicity. A zero index indicates lack of gastro-intestinal toxicity. A negative index indicates an improved melaena index during the trial.

| Results | Group | Melaena Index |
|---|---|---|
|  | Controls | 0 |
|  | Copper indomethacin | −100 |
|  | Phenylbutazone | +65 |

EXAMPLE 11

Comparative Toxicity Trial in Dogs

Ulcerogenic Index (measurement of area in $cm^2$ of gastro-intestinal ulceration of autopsy) was used to compare gastro-intestinal toxicity of identical doses of the inventors' formulation of copper indomethacin and indomethacin in an identical paste vehicle. Dosage range for both drugs was from 3× to 5× the therapeutic dose of indomethacin recommended for humans on a mg/Kg basis, and 7× to 11× the inventors' therapeutic dose of copper indomethacin.

| Results: | Mean No. of ulcers | Ulcerogenic Index |
|---|---|---|
| Copper indomethacin | 4 | 1.12 |
| Indomethacin | 4.75 | 2.16 |

EXAMPLE 12

Clinical Trials in Humans

The inventor's formulation of copper indomethacin was administered orally to a group of adult men suffering from various types of arthritis and bursitis. There was clinical remission of symptoms and improved mobility, and none reported any symptoms of gut disturbance. One, a 53 year-old bricklayer who had arthritis and bursitis in the right elbow unresponsive to other medication, was able to return to his trade.

INDUSTRIAL APPLICABILITY

It should be clear that the product, process and method of treatment will find wide use in the veterinary and medical fields.

The foregoing describes only some embodiments of the present invention and modifications obvious to those skilled in the art can be made thereto without departing from the scope of the invention.

REFERENCES

Flower, R. J., Moncado, S., and Vane, J. R. (1985) Analgesic-Antipyretics and Anti-Inflammatory Agents: Drugs employed in the treatment of gout. In: "The Pharmacological Basis of Therapeutics" 7th Ed. Eds Gilman, A. G., Goodman, L. S., Rall, T. W., and Murad, F. MacMillan, New York, 1985.

Shay, H. Gastroenterology 5 43 (1945)

Sorenson, J. R. (1), Journal of Medicinal Chemistry 19 135 (1976)

Sorenson, J. R. (2), Biol. Trace Elements Res. 5 257 (1983)

We claim:

1. A process for the preparation of an indomethacin salt of a divalent metal capable of forming a stable complex with indomethacin comprising forming a solution of indomethacin and of a salt of said divalent metal in a tertiary amide of the following formula:

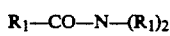

or in an N-substituted lactam of the following formula:

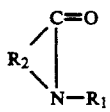

wherein $R_1$ is an alkyl having from 1 to 4 carbon atoms, and each $R_1$ may be the same or different, and $R_2$ is a cycloalkyl having from 3 to 5 carbon atoms, adding a $C_{1-4}$ alkanol or $C_{3-6}$ ketone to the solution to precipitate the indomethacin metal salt, and separating the precipitated indomethacin metal salt from the solution.

2. The process as defined in claim 1 wherein the divalent metal is copper, zinc, cobalt or nickel.

3. The process as defined in claim 2 wherein the divalent salt is a metal acetate monohydrate.

4. The process as defined in claim 3 wherein the divalent metal salt is a metal acetate monohydrate.

5. The process as defined in claim 1 wherein the tertiary amide or N-substituted lactam is selected from the group consisting of dimethylformamide, N-methyl-pyrrolidone, dimethyl acetamide and mixtures thereof.

6. The process as defined in claim 1 wherein the solution is formed by mixing a solution of indomethacin with a solution of the metal salt.

7. The process as defined in claim 6 wherein the indomethacin solution is warmed prior to addition to the metal salt solution to between about 30° C. and about 90° C.

8. The process as defined in claim 7 wherein the solution is warmed to about 50° C.

9. The process as defined in claim 1 wherein the solution of indomethacin and metal salt is warmed.

10. The process as defined in claim 9 wherein the solution is warmed to between about 50° and about 90° C.

11. The process as defined in claim 10 wherein the solution is warmed to about 80° C.

12. The process as defined in claim 1 wherein the alkanol or ketone is added with agitation to the solution of indomethacin and metal salt.

13. The process as defined in claim 1 wherein the alkanol is methanol, ethanol, n-propanol, isopropanol, n-butanol, sec-butanol or tert-butanol.

14. The process as defined in claim 13 wherein the alkanol is ethanol.

15. The process as defined in claim 1 wherein the ketone is acetone.

16. The process as defined in claim 1 wherein the solution of indomethacin and metal salt is allowed to stand for a period of time following addition of the alkanol or ketone.

17. The process as defined in claim 16 wherein the period of time is between about 8 hours and about 4 days.

18. The process as defined in claim 17 wherein the period of time is about 1 day.

19. The process as defined in claim 1 further comprising harvesting and washing the precipitate with the same alkanol or ketone used in the last addition step.

20. The process as defined in claim 19 further comprising drying the precipitate.

21. The process as defined in claim 1 wherein the divalent metal salt is a metal acetate monohydrate.

* * * * *

UNITED STATES PATENT AND TRADEMARK OFFICE
CERTIFICATE OF CORRECTION

PATENT NO. : 5,310,936
DATED : May 10, 1994
INVENTOR(S) : Hubertus L. Regtop et al.

It is certified that error appears in the above-indentified patent and that said Letters Patent is hereby corrected as shown below:

ON THE TITLE PAGE

Under heading [22] "Filed:", please delete "Jan. 15, 1992" and substitute --PCT Filed: May 21, 1990--.

Please insert the following additional filing information:
--[86]  PCT No.: PCT/AU90/00209
        § 371(e) Date: January 15, 1992
        § 102(e) Date: January 15, 1992
  [87]  PCT Pub. No.: WO90/14337
        PCT Pub. Date: November 29, 1990--.

Column 2, line 33, before "tertiary" insert --solution by dissolving indomethacin and a salt of said divalent metal in a--.

Column 2, lines 48-50, delete "solution by dissolving indomethacin and a salt of said divalent metal in a".

UNITED STATES PATENT AND TRADEMARK OFFICE
CERTIFICATE OF CORRECTION

PATENT NO. : 5,310,936
DATED : May 10, 1994
INVENTOR(S) : Hubertus L. Regtop et al.

It is certified that error appears in the above-indentified patent and that said Letters Patent is hereby corrected as shown below:

Column 7, line 6, delete "Trails" and substitute --Trials--.

Signed and Sealed this

Fourth Day of June, 1996

Attest:

BRUCE LEHMAN

Attesting Officer     Commissioner of Patents and Trademarks